United States Patent [19]
Yang et al.

[11] Patent Number: 5,115,567
[45] Date of Patent: May 26, 1992

[54] ELECTRIC PLASTER CAST SAW CONTROL SYSTEM

[76] Inventors: Chang-Min Yang; Chun-Mei Chou, both of No. 13-2, Lane 76, Dong-An Road, Tainan, Taiwan

[21] Appl. No.: 790,545

[22] Filed: Nov. 12, 1991

[51] Int. Cl.$^5$ .............. B27B 9/02; B23D 47/08; A61F 13/04; A61F 15/02
[52] U.S. Cl. .................... 30/166.3; 30/370; 128/317; 606/172
[58] Field of Search ............... 30/165, 370, 390, 505, 30/166.3; 606/82, 172, 176; 128/91 A

[56] References Cited
U.S. PATENT DOCUMENTS

| | | | |
|---|---|---|---|
| 4,625,405 | 12/1986 | Hudnutt | 128/317 |
| 4,637,391 | 1/1987 | Schlein | 30/166.3 |
| 4,887,598 | 12/1989 | Berke | 606/172 |
| 4,976,034 | 12/1990 | Whitman | 30/370 |

Primary Examiner—Douglas D. Watts
Assistant Examiner—Paul M. Heyrana, Sr.
Attorney, Agent, or Firm—Bacon & Thomas

[57] ABSTRACT

An electric plastic cast saw control system for cutting off of plastic cast composed of an inner layer of absorbent cotton and an outer layer formed by hardened covering material including a thin conductive plate placed between the inner layer and the outer layer so that a relay device is triggered to cut off power supply to electric saw on the instant the saw gets contact with the thin conductive plate and consequently stop the electric saw instantaneously, and a reset device to resume power supply to the electric saw automatically or manually after cutting off of the power source.

7 Claims, 5 Drawing Sheets ic PLASTER CAST SAW CONTROL SYSTEM

BACKGROUND OF THE INVENTION

This invention relates to a control system for electric plaster cast saw, particularly a control system to stop electric plastic cast saw automatically and promptly during cutting of plaster cast or other covering materials.

Human limbs may be fractured under a great external force. Infant's limbs may be deformed congenitally or acquiredly. Currently, the medical treatment dealing with bone fracture or deformity always involves wrapping of medical plaster around the injured area and allowing the plaster to harden so that the limb can be healed quickly without external influence.

After a certain period, the plaster cast surrounding the injured limb must be cut with an electric saw for removal and examination. The limb may have to receive other therapy or surgery if necessary.

In general, depth which the saw has gone into the plaster cast is judged by visual inspection, accuracy of which depends on operator's experience. Hence, skill is indispensable to avoid injury to patient's muscle. However, even sawing is carried out carefully, patent's skin or muscle may be hurt accidentally, and such kind of accident occurs frequently. Therefore, patient is always afraid of such sawing, operator may hesitate to carry out the sawing, and consequently the operation is prolonged. Accident hurt to patient's skin or muscle may happen due to unexpected movement or uncontrolled shaking of limb especially when the patient is a baby or person who has lost the capacity to control his body.

Therefore, there is an urgent need in the medical field for a controller which can stop electric saw automatically as soon as the plaster cast is cut off.

SUMMARY OF THE INVENTION

The main object of the present invention is to provide a control system for electric plaster cast saw to stop electric saw automatically on the instance the plaster cast is cut off in order to prevent from injury to patient's skin or muscle.

Another object of the present invention is to provide a control system for electric plaster cast saw which can effectively prevent from injury to patient's skin or muscle, and hence the patent's fear can be eliminated, operator's confidence for safe operation is improved, and unnecessary dispute can be avoided.

Another object of the present invention is to provide a control system for electric plaster cast saw which can cut off power supply and stop electric saw automatically on the instant the plaster cast is cut off so that cutting off of plater cast can be performed by any nurse or operator and then work burden of experienced nurse or surgeon can be relieved.

The electric plaster cast saw control system according to the present invention include a thin conductive plate between the plaster layer and absorbent cotton layer of each plastic cast with an extended end of the thin conductive plate exposed outside the plastic cast so that it can be connected to the control system by a conductive wire. On the instant the electric saw gets contact with the thin conductive plate, a relay is triggered to trip from its normal closed contact to normal open contact, and consequently cut off power supply to the electric saw instantaneously. The electric saw is hence stopped immediately to prevent from injury to patient's skin or muscle. The control system has also a reset device to resume power supply to the electric saw, and a warning device to give audible or visible warning signal.

BRIEF DESCRIPTION OF THE DRAWINGS

These and other objects and features of the invention will become more apparent from the following description taken in connection with the accompanying drawings wherein.

DETAILED DESCRIPTION OF THE PREFERRED EMBODIMENT

Figure 1:
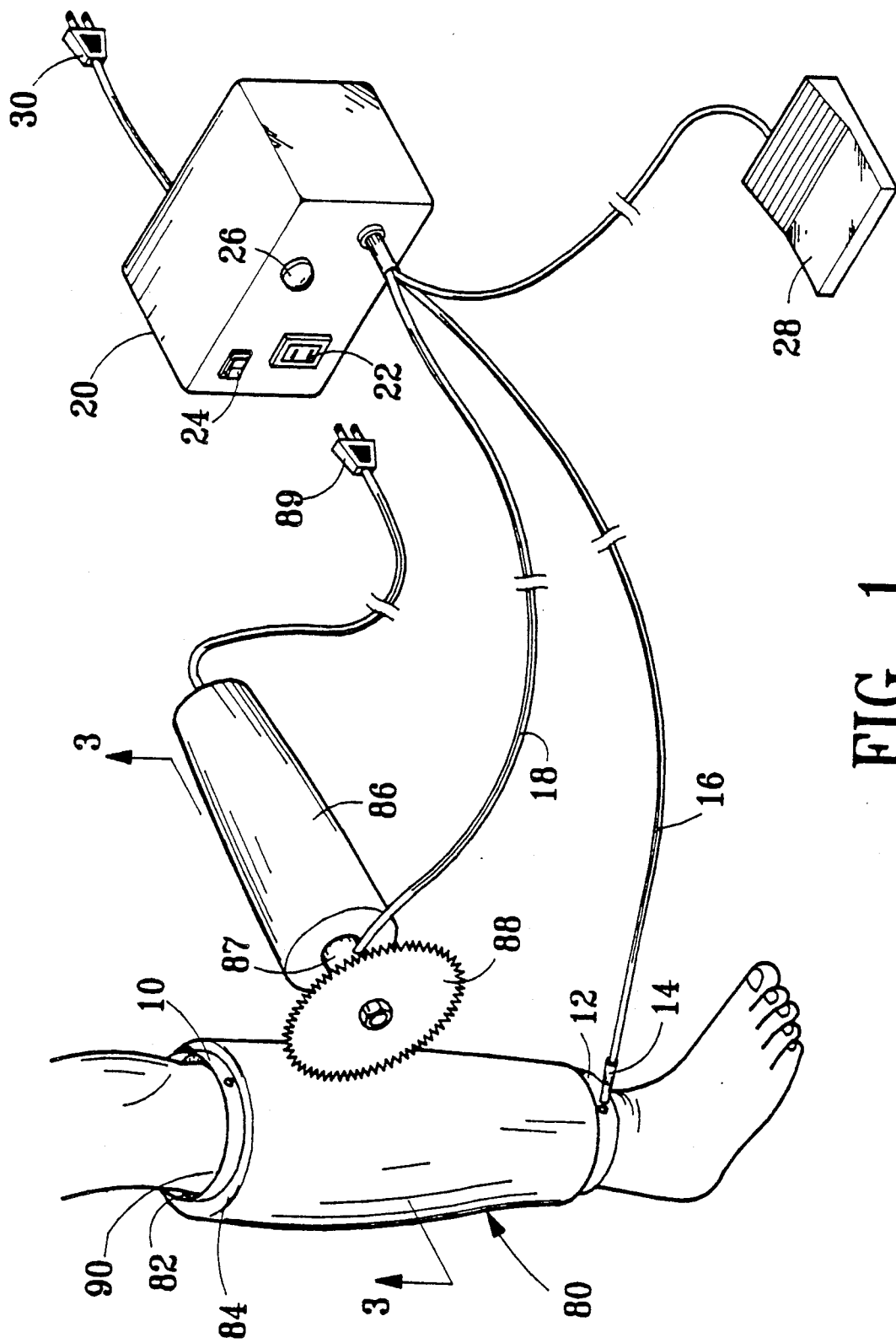
FIG. 1 is a perspective view of the first embodiment of the electric plaster cast saw control system according to the present invention.
Figure 3:
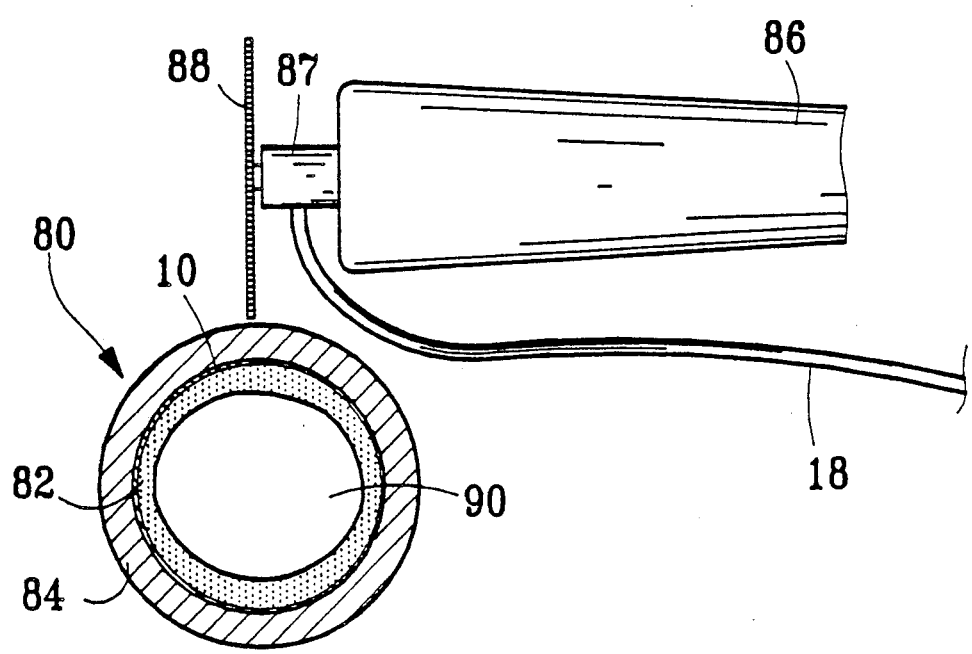
FIG. 3 is a sectional view taken along line 3—3 in FIG. 3.

Referring to FIGS. 1 and 3, each plaster cast 80 to wrap patient's fractured limb 90 has an inner layer 82 composed tearable absorbent cotton to contact with patient's skin, an outer layer 84 composed of a covering material which is hardened upon contact with water, normally plaster or resin for medical purpose, and a thin conductive plate 10 located between the inner layer and the outer layer. The thin conductive plate 10 is made of electric conductive material such as tin foil or aluminum foil which does not affect X-ray reading or diagnosis. The thin conductive plate 10 has an extended end 12 extended outside the plaster cast 80. The extended end 12 is designed to connect to a control system located in a power control box 20 by means of a clamp 14 and a conductive wire 16. An electric saw 86 to cut off the outer layer 84 comprises a high speed motor (not shown in the figures) and a circular saw blade 88 fixed to a shaft 87 of the motor. The shaft is connected to the control system in the control box 20 with a conductive wire 18 to form a control circuit. The electric saw 86 is connected to a socket 22 on the control box 20 with a plug 89 for an electric power to operate the electric saw 86. The control system in the control box 20 is incorporated with a selector switch 24, a warning device 26, and a reset pedal 28. The control box 20 is connected to an external power source with a plug 30. The warning device 26 is an electric or electronic alarm to give audible or visible warning signal. The warning device is preferably installed on the surface of the control box 20 or the electric saw 86 or other appropriate location so that it can be seen during the sawing process.

Figure 2:
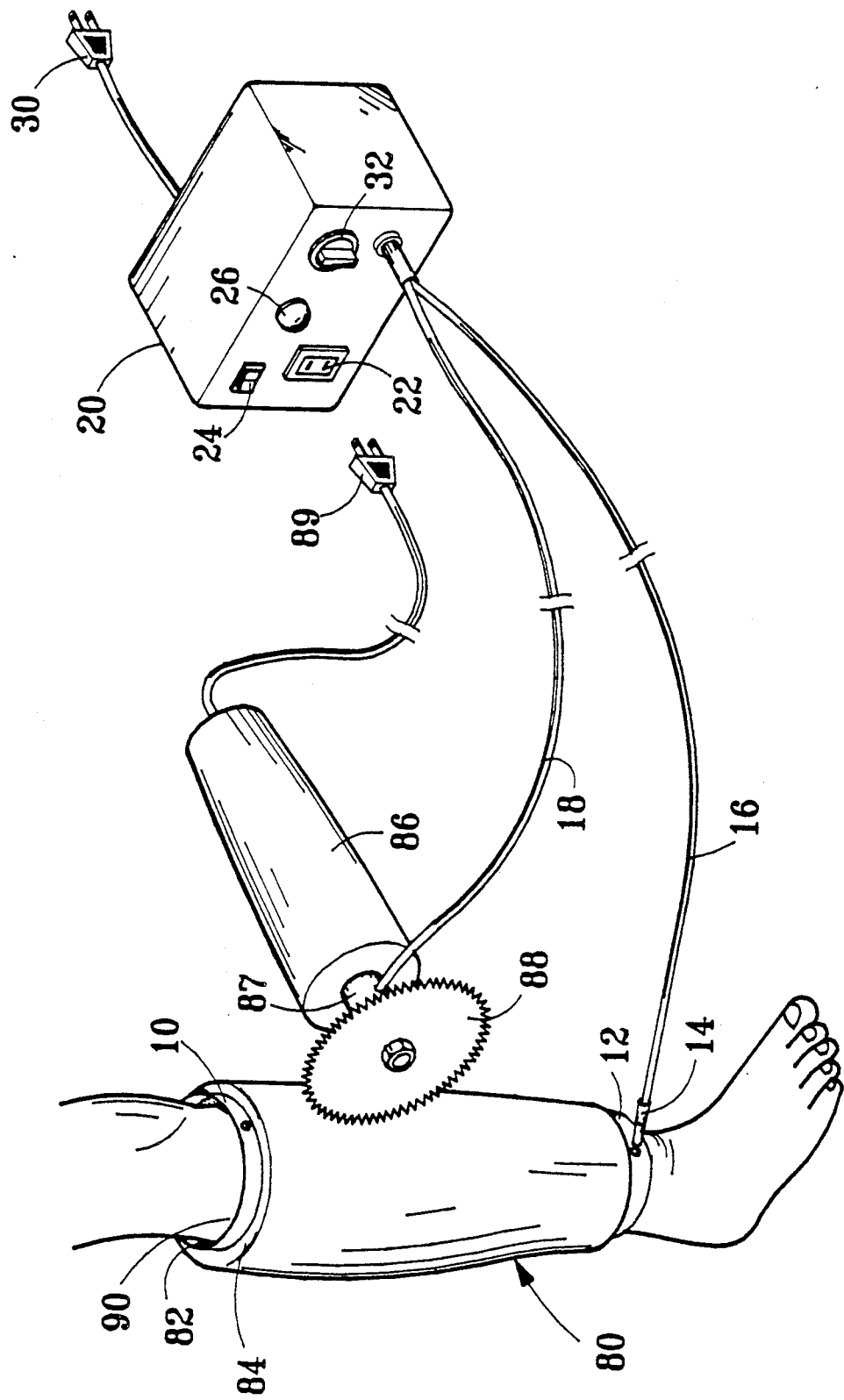
FIG. 2 is a perspective view of the second embodiment of the electric plaster cast saw control system according to the present invention, in which an automatic reset device is used to replace the manual reset device shown in FIG. 1

Please refer to FIG. 2 for the second embodiment of the control system for plaster cast saw according to the present invention. It is same with the embodiment shown in FIG. 1 except a reset knob 32 is used instead of the reset pedal 28.

Figure 4:
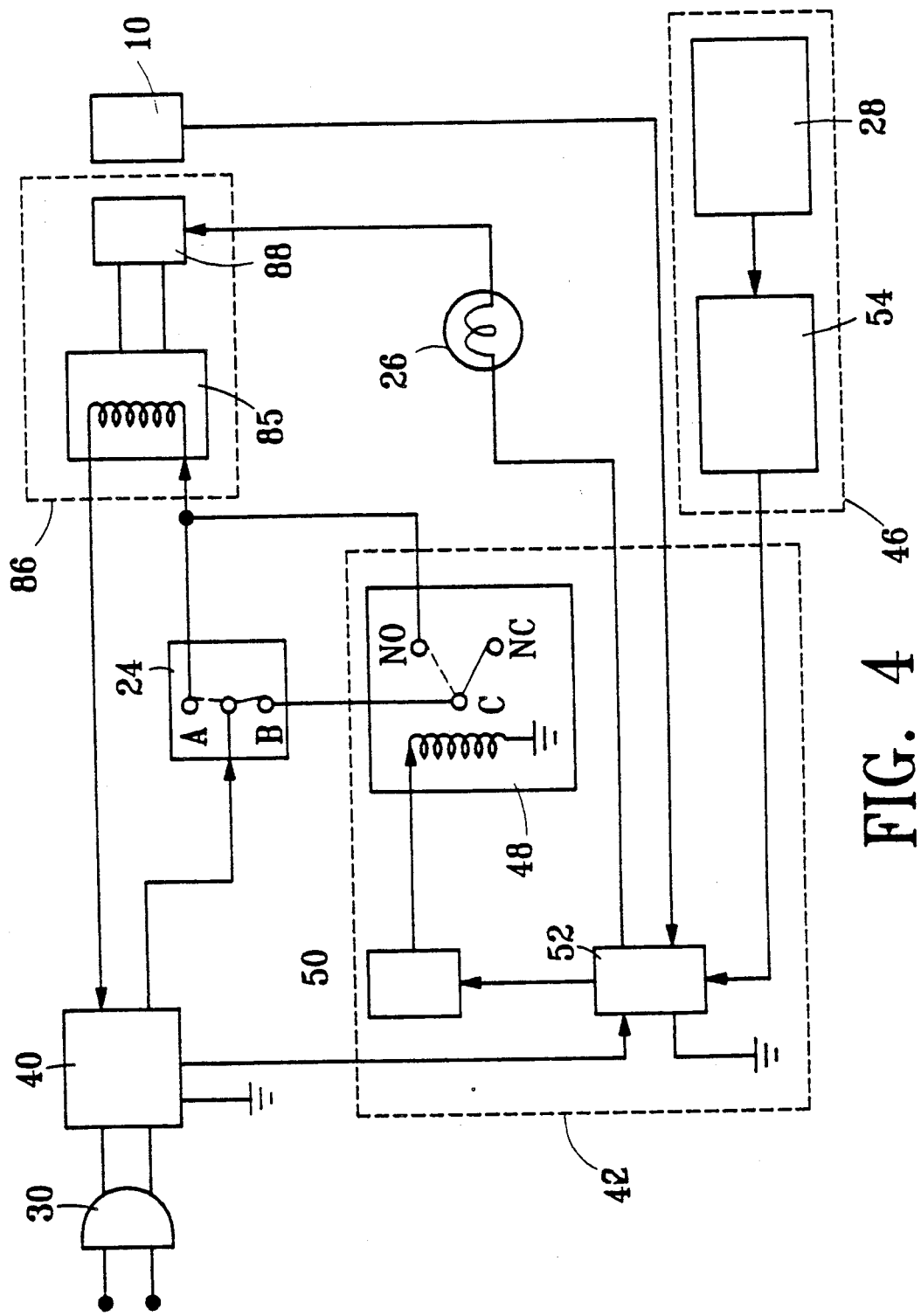
FIG. 4 is a block diagram for the first embodiment of the present invention.

Please refer to FIG. 4 for a block diagram for the first embodiment of control system for plaster cast saw according to the present invention. The control system comprises a power supply 40, a selector switch 24, a relay device 42, a warning device 26, and a reset device 46. The relay device 42 is composed of a relay 48, a driver 50 and a control circuit 52 to cut off power supply to the electric saw 86 instantaneously as soon as the saw blade 88 gets contact with the thin conductive plate 10. The reset device 46 is composed of the reset pedal 28 and a reset circuit 54 to restart the electric saw 86. The power supply 40 is connected to an external power source for provision of electric power to the electric saw 86 directly, or to the electric saw 86 through the relay device 42 by selection of its operator. If the selector switch 24 is located at the first contact A, the electric saw is started directly for continuous operation, the relay device 42, the warning device 26 and the reset device 46 do not function. If the selector switch 24 is located to the second contact B, the power source is not provided to the electric saw directly, but is connected to a common contact C for the relay 48 which is normally closed at NC so that the electric saw 85 can not be operated. The power source 40 also provides an electric power to the control circuit 52 so that the control circuit is ready to receive signal and upon triggering of the reset device 46 by stepping the reset pedal 28, which causes the reset circuit 54 to trigger the control circuit 52, start the driver 50 to drive to relay 48 to trip from the normal closed contact NC to a normal open contact NO, and consequently the power supply 40 provides the electric saw 86 with an electric power through the common contact C and the normal open contact NO for operation of the electric saw 86. By this way, the electric saw 86 can be operated to cut off plaster cast. Whenever the saw blade 88 gets contact with the thin conductive plate 10 after cutting off of the outer layer 84, the saw blade 88, the thin conductive plate 10, the warning device 26 and the control circuit 52 become a closed loop, the warning device 26 is activated to give a warning light or voice, the control circuit 52 cut off the driver 50 instantaneously so that the relay 48 trips from the normal open contact NO to the normal closed contact NC to cut off power supply to the electric saw 86, and consequently, the electric saw 86 is stopped immediately. Hence, the patent's skin or muscle can be prevented form hurting by the saw blade 88. To restart the electric saw 86, only the reset pedal 28 has to be stepped so that, as described above, the reset circuit 54 triggers the control circuit 52 again to cause the driver 50 to drive the relay 48 to trip from the normal closed contact NC to the normal open contact NO, and start the electric saw 86 again.

The relay 48 of can be of solid state or mechanically controlled. The warning device shown in the figures is a warning indicator. It can be replaced by a buzzer to provide audible warning signal.

Figure 5:
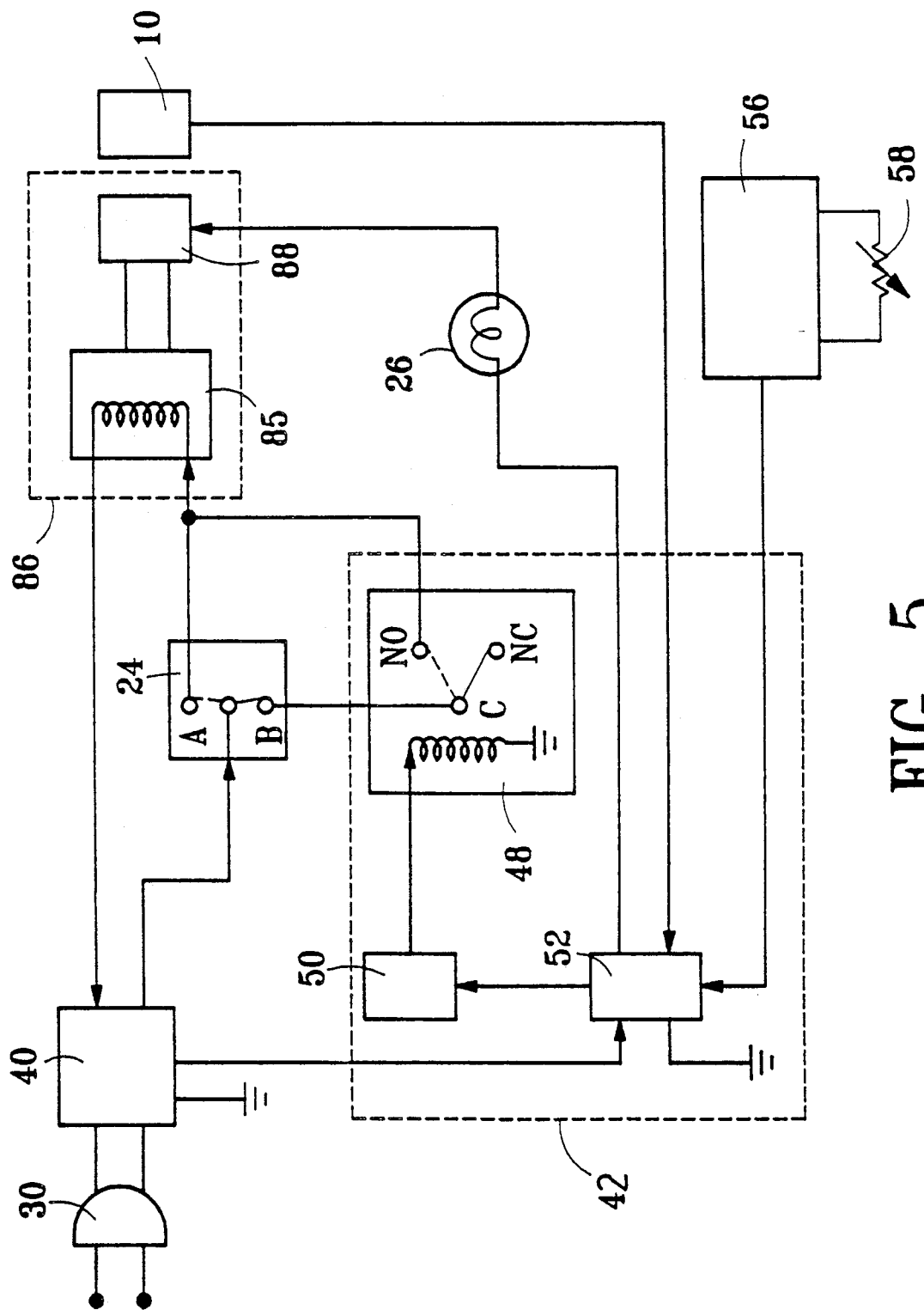
FIG. 5 is a block diagram for the second embodiment of the present invention.

Please refer to FIG. 5, a block diagram for the second embodiment of the present invention, the plug 30, the power supply 40, the selector switch 24, the relay control device 42, the warning device 26, the electric saw, and the thin conductive plate 10 are same with that used in the first embodiment shown in FIG. 4, but an automatic reset device 56 is used instead of the reset device 46 in FIG. 4. The automatic reset device 56 can be an adjustable pulse generator which is triggered to send a pulse to the relay device 42 on the instant that the saw blade 88 gets contact with the thin conductive plate 10. Upon input of the pulse, the relay 48 trips from the normal open contact NO to the normal closed contact NC, and consequently the power supply to the electric saw 86 is cut off, the patent's skin or muscle can be prevented form hurting by the saw blade 88. After elapse of a delay time caused by the pulse, the relay 48, in the absence of pulse input, trips from the normal closed contact NC to the normal open contact NO, and consequently power supply to the electric saw 86 is resumed to continue the operation. The length of the delay time can be adjusted by a variable resistor 58. The reset knob 32 on the control box 20 can be turned to adjust resistance of the variable resistor, and consequently adjust the length of delay time.

Procedures to operate the first embodiment of the electric plaster cast saw control system according to the present invention are described below:

(1) Connect the control box to an external power source with the plug 30.
(2) Connect the electric saw 86 to the control box 20 by inserting the plug 89 to the socket 22.
(3) Attach the conductive wire 16 to the extended end 12 of the thin conductive plate with the clamp 14, and attach another end of the conductive wire 16 to the electric saw 86.
(4) Set the selector switch 24 to contact B position.
(5) Step the reset pedal 28 to start the electric saw 86. The indicator of the warning device 26 is off at this instant, which means that the control box 20 is in good working condition.
(6) Cut off the outer layer 84 of the plaster cast 84 by the electric saw 86. The power source is cut off and the electric saw is stopped immediately, and the indicator of the warning device 26 is on to warn the operator not to operate the electric saw 86 on the instant the saw blade 88 gets contact with the thin conductive plate 10 so that the patent's skin or muscle can be prevented form hurting by the saw blade 88.
(7) If required, step the reset pedal 28 to resume operation of the electric saw 86. The indicator of the warning device 26 is off when the reset pedal 28 is stepped.
(8) Repeat steps (6) and (7) till the plaster cast is completely cut off.
(9) If operation of the electric saw 86 without control of the control system according to the present invention, set the selector switch 24 at the contact A position, then the electric saw 86 is operating continuous and will not stop when the saw blade 88 gets contact with the thin conductive plate 10.
(10) It is recommendable to explain and demonstrate the patient the whole operating process before sawing is started.

Procedures to operate the second embodiment of the electric plaster cast saw control system according to the present invention are described below:

(1) through (4) are same with that for the first embodiment.
(5) Turn the reset knob to select the desired length of delay time for interruption of the electric saw 86.
(6) Cut off the outer layer 84 of the plaster cast 80 by the electric saw 86. The power source is cut off and the electric saw 86 is stopped immediately, and the indicator of the warning device 26 is on to warn the operator not to operate the electric saw 86 on the instant the saw blade 88 gets contact with the thin conductive plate 10 so that the patent's skin or muscle can be prevented form hurting by the saw blade 88.

(7) After elapse of the delay time, power supply to the electric saw 86 is resumed, the electric saw 86 is started again, the indicator of the warning device 26 is off.

(8) Repeat steps (6) and (7) till the plaster cast is completely cut off.

(9) If operation of the electric saw 86 without control of the control system according to the present invention, set the selector switch 24 at the contact A position, then the electric saw 86 is operating continuous and will not stop when the saw blade 88 gets contact with the thin conductive plate 10.

(10) It is recommendable to explain and demonstrate the patient the whole operating process before sawing is started.

While cutting off plaster cast with the control system according to the present invention, the power supply to the electric saw is cut off instantaneously on the instant the saw blade gets contact with the thin conductive plate, and consequently, the electric saw is stopped, and the patent's skin and muscle is prevented from hurt which may be caused by the saw blade. With such an invention, the patent's fear can be eliminated, the operator has confidence to remove the plaster cast safely, and consequently the time required to remove the plaster cast can be shortened. Moreover, the with the present invention, the electric saw can be operated by any nurse or operator, and hence work burden of surgeon or experienced nurse can be reduced.

Many changes and modifications in the above described embodiment of the invention can, of course, be carried out without departing from the scope hereof. Accordingly, to promote the progress in science and the useful arts, the invention is disclosed and is intended to be limited only by the scope of the appended claims.

What is claimed is:

1. An electric plastic cast saw control system for cutting off of plastic cast composed of an inner layer of absorbent cotton and an outer layer formed by hardened covering material, comprising a thin conductive plate located between the inner layer and the outer layer;

a relay device to cut off power supply to electric saw on the instant the thin conductive plate is contacted by saw blade of the electric saw; and a reset device to drive the relay device to resume power supply to the electric saw after the power supply is cut off.

2. An electric plastic cast saw control system as claimed in claim 1 which further includes a warning device to give visible warning signal on the instant the saw blade gets contact with the thin conductive plate.

3. An electric plastic cast saw control system as claimed in claim 1 which further includes a warning device to give audible warning signal at the instance the saw blade gets contact with the thin conductive plate.

4. An electric plastic cast saw control system as claimed in claim 1 which further includes a selector switch for selection of direct connection of the power source to the electric saw so that the electric saw is free from the control of the relay device.

5. An electric plastic cast saw control system as claimed in claim 1 which further include a reset device composed of a reset circuit to trigger the relay device to resume power supply to the electric saw after the power supply is cut off, and a pedal to activate the reset circuit.

6. An electric plaster cast saw control system as claimed in claim 5 wherein the reset device is a pulse generator which is triggered to send a pulse to the relay device on the instant that the saw blade gets contact with the thin conductive plate to stop power supply to the electric saw for a certain delay time, and to resume power supply to the electric saw after the end of the delay time.

7. An electric plastic cast saw control system as claimed in claim 5 wherein the delay time of the pulse generated by the pulse generator can be adjusted by a variable resistor.

* * * * *